United States Patent [19]

Kimura et al.

[11] Patent Number: 5,102,882
[45] Date of Patent: Apr. 7, 1992

[54] PYROGLUTAMIDE DERIVATIVES

[75] Inventors: Koyishi Kimura, Takatsuki; Shoichi Chokai, Kameoka; Toshio Tomita, Kusatsu; Masahiro Kise, Kyoto; Kenichi Nakamura, Nagaokakyo, all of Japan

[73] Assignee: Nippon Shinyaku Co., Ltd., Japan

[21] Appl. No.: 661,523

[22] Filed: Feb. 26, 1991

Related U.S. Application Data

[63] Continuation of Ser. No. 286,652, Dec. 19, 1988, abandoned, which is a continuation of Ser. No. 5,255, Jan. 20, 1987, abandoned.

[30] Foreign Application Priority Data

Jan. 21, 1986 [JP] Japan ................................ 61-011359
Jan. 21, 1986 [JP] Japan ................................ 61-011360
Jul. 24, 1986 [JP] Japan ................................ 61-175168

[51] Int. Cl.$^5$ ................... A61K 31/535; C07D 265/28
[52] U.S. Cl. ..................... 514/235.5; 514/210;
514/212; 514/218; 514/222.2; 514/222.5;
514/222.8; 514/234.2; 514/234.5; 514/255;
514/326; 514/343; 514/235.8; 548/518;
548/519; 540/575; 540/607; 540/480; 544/60;
544/141; 544/372; 546/208
[58] Field of Search ............... 548/318, 519; 540/575,
540/602, 480; 544/60, 141, 372; 546/208;
514/210, 212, 218, 222.2, 222.5, 222.8, 234.2,
234.5, 255, 326, 343, 235.5, 235.8

[56] References Cited

U.S. PATENT DOCUMENTS

| | | | |
|---|---|---|---|
| 3,051,722 | 8/1962 | Biel | 260/319 |
| 4,077,951 | 3/1978 | Loffet | 260/112.5 R |
| 4,483,991 | 11/1984 | Freed | 546/189 |
| 4,525,476 | 6/1985 | Butler | 514/326 |

Primary Examiner—Robert T. Bond
Attorney, Agent, or Firm—Rosenman & Colin

[57] ABSTRACT

Pyroglutamide derivatives have been found to be useful as nootropic agents for administration to humans and animals.

24 Claims, No Drawings

PYROGLUTAMIDE DERIVATIVES

This is a continuation of Ser. No. 286,652 filed Dec. 19, 1988, now abandoned which is a continuation of U.S. Ser. No. 005,255 filed Jan. 20, 1987, now abandoned.

The present invention relates to pyroglutamide derivatives, pharmaceutical compositions containing said derivatives as the active agent, to methods of producing nootropic effects in humans and animals by administering said derivatives, and to methods for the production of such derivatives.

More particularly the present invention relates to pyroglutamide derivatives of the formula

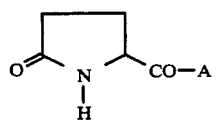

or pharmaceutically acceptable acid addition salts thereof wherein A is a cyclic amino moiety having one or more nitrogen heteroatoms, said moiety being unsubstituted or substituted by a substituent selected from the group consisting of alkyl, diarylalkyl, aralkyl, aryl, hydroxyalkyl, hydroxy, alkanoyl, aralkylcarbonyl, aralkyloxycarbonyl, aralkenylcarbonyl, arylcarbonyl, heterocyclyl carbonyl, alkoxycarbonyl, aminoalkyl, aminoalkylcarbonyl, aminocarbonyl, carbamoylalkyl, carbamoyalkylcarbonyl, oxo, heterocyclyl, aryloxyalkyl, and alkanoylamino, said alkyl being a lower alkyl moiety, said alkenyl being a lower alkenyl moiety; said alkoxy being a lower alkoxy moiety; said aryl being unsubstitued or substitued by 1 or more of the same or different substitutents selected from the group consisting of lower alkyl, lower alkoxy, aryl loweralkyloxy, lower alkanoyl, lower alkoxycarbonyl, halo, halo loweralkyl, nitro and methylenedioxy; said heterocyclyl moiety being a 4–8 membered ring having one or two heteroatoms selected from the group consisting of nitrogen, oxygen and sulphur, and wherein when one of the above substituents contains an amino moiety, said amino moiety is straight chain amino or a 4–8 membered nitrogen containing ring wherein the nitrogen atom is the only heteroatom or such a ring containing 1 or more additional heteroatoms selected from the group consisting of nitrogen, sulphur and oxygen, said amino moiety being unsubstituted or substituted by one or more substituent selected from the group consisting of lower alkyl, aryl lower alkyl, aryl lower alkyloxycarbonyl and carbomayl provided that A is not 2,2,6,6-tetramethylpiperidino, 2-phenyl-3-methylmorpholino, 3-hydroxypiperidino, 4-hydroxypiperidino, 2-aminocarbonyl-pyrrolidino, unsubstituted pyrrolidino, piperidino, morpholino, or thiomorpholino.

As a result of an increase in the number of elderly people in the total population there has been a marked increase in attention to the treatment of cognitive problems associated with Alzheimer's disease and other age-related disturbances. Brain metabolism activators, cerebral blood flow improving agents, tranquilizers, cholinergic agents and the like have been studied but none have been found to be effective. Recently, compounds such as aniracetam and pramiractam have been examined as nootropic agents. In Japanese Laid Open Applications 52/125166 and 51/115472, TRH (thyrotropin releasing hormones)-like compounds have been described.

The present invention is concerned with the discovery of novel nootropic agents and to the use of certain specific pyroglutamide derivatives as nootropic agents some of which specific derivatives were heretofore only known to be useful as intermediates. Therapeutic utility for the compounds of the present inventions includes the treatment of senile dementia, dementia caused by retarded mental growth, after effects of encephalitis, cerebral convulsion, cerebral apoplexy, cerebral arteriosclerosis, brain wounds and the like.

More particularly, those pyroglutamide derivatives of the formula I where A is other than 2,2,6,6-tetramethylpiperidino, 2-phenyl-3-methylmorpholino, 3-hydroxypiperidino, 4-hydroxypiperidino, 2-aminocarbonylpyrrolidino, unsubstitued pyrrolidino, unsubsited piperidino, unsubstitued morphorino or unsubstited thiomorpholino are novel substances per se.

Those pyroglutamide derivatives wherein A is unsubstituted pyrrolidino, unsubstitued piperidino, unsubsited morpholino or unsubstituted thiomorpholino were hitherto known as intermediates and their embodiment in pharmaceutical compositions according to the present invention and methods of affecting nootropic action in humans and animals is novel. U.S. Pat. No. 3,051,722 describes 5-pyrrolidone-2-carboxamides. U.S. Pat. No. 4,077,951 describes L-pyroglutamyl-L-prolinamide.

Japanese Laid Open Applications 51/8266 and 49/14462 describe N-piperidinopyroglutamides and N-pyrrolidinopyroglutamides as intermediates useful for producing antiulcer compounds. Said pyroglutamides are also disclosed as intermediates in Japanese Laid Open Application 14462/74.

According to the present invention, preferred cyclic amino moieties for A are those containing 4–10 ring members and having one or 2 nitrogen heteroatoms. Specific examples include: azetidino, pyrrolidino, piperidino, azepino, azocino, piperazino, homopiperazino and the like.

When a cyclic amino group is substited by a substitutents which contains an aryl moiety, the aryl moiety is unsubstituted or substited by one or more of the same or different alkyl, alkoxy, aralkyloxy, alkanoyl, alkoxycarbonyl, halo, haloalkyl, nitro, or methylenedioxy wherein the alkyl and alkoxy moieties are preferably lower alkyl or lower alkoxy moieties.

When the cyclic amino group is substited and the substituent contains an amino group, such amino group itself may form a 4–8 membered nitrogen containing ring wherein the amino nitrogen atom is to only heteroatom or it may contain one or two additional heteroatoms selected from the group consisting of oxygen, sulphur and nitrogen. Said amino group may itself be substituted by one or more of the same or different alkyl moieties, preferably lower alkyl moieties. Examples of such cyclic amino moieties are pyrrolidino, piperidino, azepino, piperazino, morpholino, thiomorpholino and the like. The amino groups may be unsubstited or substituted with one or more of the same or different substituents selected from the group consisting of alkyl, aralkyl, aralkyloxycarbonyl and carbamoyl wherein the alkyl moieties are preferably lower alkyl moieties.

According to the present invention, preferred lower alkyl moieties are those containing 1 to 4 carbon atoms and include straight or branched chain moieties, i.e., methyl, ethyl, n-propyl, isopropyl, n-butyl, isobutyl, sec-butyl and tertbutyl.

According to the present invention diarylalkyl moieties preferably are diphenyl moieties which contain alkyl moieties of 1-4 carbon atoms such as diphenylmethyl, diphenylethyl, diphenylpropyl, diphenylbutyl and the like.

Preferred aralkyl moieties according to the present invention are those of 7-12 carbon atoms for example benzyl, phenethyl, phenylpropyl, naphthylmethyl, naphthylethyl and the like.

Preferred aryl groups according to the present invention are those of 6 to 14 carbon atoms and include phenyl, α-naphthyl, β-naphthyl, anthryl, biphenyl and the like.

Preferred hydroxyalkyl moieties according to the present invention are those wherein the alkyl moiety contains 2-4 carbon atoms for example 2-hydroxyethyl, 3-hydroxypropyl, 4-hydroxybutyl, and 2-hydroxypropyl. The hydroxy moiety may be at any position on the alkyl chain.

Preferred alkanoyls according to the present invention are those of 1-7 carbon atoms including formyl, acetyl, propionyl, butyryl, isobutyryl, valeryl, isolvaleryl, pivaroyl, hexanoyl, heptanoyl and the like.

Preferred aralkenylcarbonyls according to the present invention are those of 8-10 carbon atoms including, for example, cinnamoyl.

Preferred heterocyclic moieties according to the present invention are those containing 4-8 ring members and having heteroatoms selected from the group consisting of nitrogen, oxygen and sulphur.

Preferred heterocycles are 2-pyridyl, 3-pyridyl, 4-pyridyl, 2-thienyl, 3-thienyl, 2-furyl, 3-furyl, morpholino, and thiomorpholino.

It is preferred that the alkoxy moieties according to the present invention be straight or branch chain and contain from 1-5 carbon atoms, for example, methoxy, ethoxy, n-propoxy, isopropoxy, n-butoxy, isobutoxy, sec-butoxy, tert-butoxy, n-pentyloxy, or iso-pentyloxy.

The preferred aminoalkyl moieties, the preferred aminoalkylcarbonyl moieties, the preferred carbamoylalkyl and the preferred carbamoylalkylcarbonyl moieties according to the present invention are those wherein the alkyl group contains 1-3 carbon atoms for example methyl, ethyl, n-propyl, and isopropyl.

The preferred halo moieties according to the present invention include chloro, bromo, fluoro and iodo.

The preferred haloalkyl moieties according to the present invention are those containing 1-3 halo atoms and 1-3 alkyl moieties. Trifluoromethyl is particularly preferred.

The compounds of the present invention may be produced according to the following methods:

Method A:

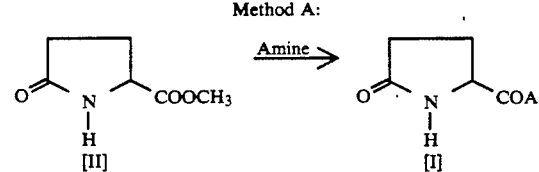

Method B:

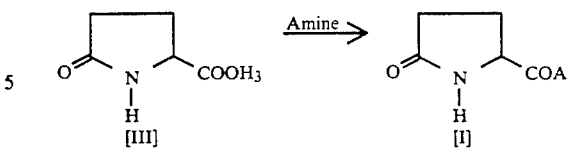

Method C:

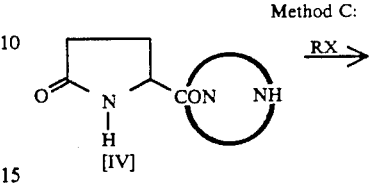

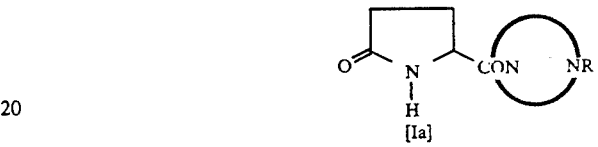

wherein R is a substituent for the group A as above defined and X is halo.

Method D:
Acid Halide or Carboxylic Acid, DCC

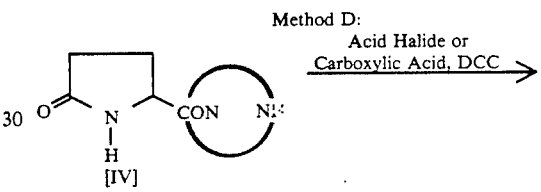

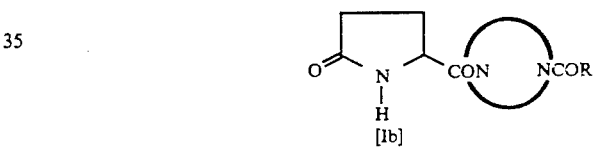

wherein COR' is an acyl residue substituent for the group A.

Method E:
Halogenated Acid Halide

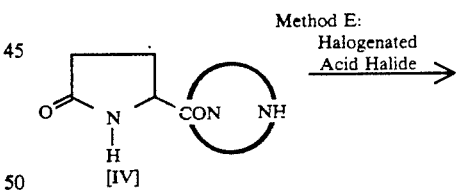

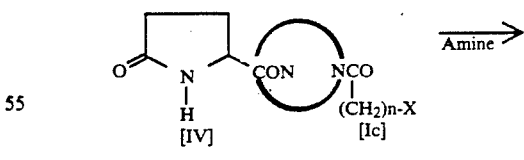

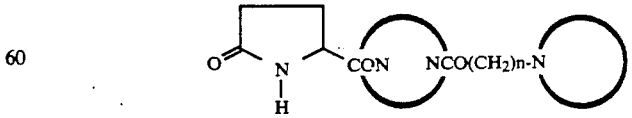

wherein is straight chain or cyclic amino, n is an integer of 1-3 and X is halo.

With further reference to each of the above methods, applicants believe that it is preferable to use the reaction conditions and reactants as set forth below.

METHOD A

Various amines may be reacted with compound II to produce compounds of the formula I according to the present invention. This amidation reaction may be conducted using procedures per se known. For example, not less than equimolar (preferably 1.0-1.3 molar) amine to the compound of the formula II is used and the reaction may be done at about 50° to 160° C. and, preferably, at about 90° to 120° C. Most conveniently, the reaction may be conducted at the boiling point of the solvent used.

As to the solvent, any inert solvent may be used. Suitable solvents include alcohol type solvents (such as methoanol, ethanol, isopropanol, and the like), halogenated hydrocarbon type solvents (such as chloroform, carbon tetrachloride, and the like), aromatic hydrocarbon type solvents (such as benzene, toluene, xylene and the like), either type solvents (such as tetrahydrofuran, dioxane, and the like) or aprotic polar solvents (such as N, N-dimethylformamide and the like). The reaction may be conducted in the absence of the solvent.

METHOD B

Various amines may be reacted with compound III to produce compounds of the formula I according to the present invention. This amidation reaction may be conducted using procedures per se known. For example, various amines are condensed directly with compounds of the formula III using dicyclohexylcarbodiimide (DCC) or diphenylphosphorylazide (DDPA); or reactive derivatives of the compound III such as, for example, an acid anhydride, imidazolide or mixed acid anhydride—anhydride with methyl carbonate, anhydride with ethyl carbonate, anhydride with iso-butyl carbonate, etc. are subjected to the reaction A method using an activated ester may also be used. When condensation agents such as DCC are used, the reaction may be preferably carried out in a suitable solvent for example, halogenated hydrocarbons such as methylene chloride, chloroform, etc., ether type solvents such as tetrahydrofuran, dioxane, etc., acetonitrile, N, N-dimethylformamide, and the like at about −30° to about 180° C. It is preferred to use equimolar to a little in excess of compound III to one mole of amine when DCC is used.

In the case of compounds of the formula I wherein A is a cyclic amino group which contains more than one nitrogen heteroatom and said nitrogen is substituted, such compounds may be produced by alkylating, acylating or aminating a compound produced according to processes A and B. Methods C-E described below may thus be used.

METHOD C

Compounds of the formula Ia may be produced by alkylation of compounds of the formula IV obtained according to methods A or B above. This alkylation reaction may be carried out by procedures per se known. Suitable alkylating agents include those used in conventional alkylation reactions. For example corresponding alkyl halides such as chloride, bromide, iodide, and the like, sulfuric acid esters, sulfonic acid ester, and the like may be used. When alkyl halides are used, the reaction is preferably conducted in a suitable solvent such as, for example, alcohols such as methanol, ethanol, etc.; ethers such as tetrahydrofuran, dioxane, etc.; halogenated hydrocarbons such as methylene chloride, chloroform, etc.; aromatic hydrocarbons such as benzene, toluene, etc.; aprotic polar solvents such as acetonitrile, N,N-dimethylformamide, etc.; or mixtures thereof, at room temperature to the boiling point of the reaction solvent in the presence of a base such as, for example, sodium bicarbonate, potassium carbonate, pyridine, trialkylamine, and the like.

In that case, it is preferred to use an equivalent or a greater quantity of alkyl halide to compound IV. In order to increase the yield and to accelerate the reaction, catalytic amounts (0.01 to 0.1 mole equivalent) of sodium iodide or potassium iodide may be added.

METHOD D

Acylation of the compounds of the formula IV obtained according to Methods A or B gives compounds of the formula Ib. This acylation reaction may be conducted by methods substantially the same as Method B or the reaction of the acid halide with the compound IV may also be used.

When an acid halide is used, the reaction is, usually conducted in a solvent, for example, ethers such as tetrahydrofuran, dioxane, etc.; halogenated hydrocarbons such as methylene chloride, chloroform, etc.; aromatic hydrocarbons such as benzene, toluene, etc.; aprotic polar solvents such as acetonitrile, N,N-dimethylformamide, etc.; water; or a mixture thereof at about −10° to about 100° C. in the presence of a base such as, for example, sodium bicarbonate, potassium carbonate, sodium hydroxide, potassium hydroxide, pyridine, trialkylamine, etc.

In this case, the amount of the acid halide is preferably the same or greater than that of the compound IV.

METHOD E

Compounds of the formula Ic may be produced by the acylation of compounds of the formula IV obtained according to Methods A or B followed by the reaction with an amine. Such reactions may be conducted as described according to Methods D or E.

When diamines such as piperazine are used in the above manufacturing methods, one of the amines is protected by known methods followed by the reaction with compounds II or III and then the protective group is removed to yield compound I.

Compounds II and III used as starting materials in the above methods are commercially available. Similarly, the amines may also be commercially available or may be manufactured by known methods.

The compounds I obtained by the above methods may be isolated in the form of the free base by a method known per se. For example, separation/purification may be carried out by concentration, conversion of the liquid property, dissolution into another phase, extraction with solvent, crystallization, recrystallization, fractional distillation, chromatography, or the like.

It is also possible to isolate the compound in the form of an acid-addition salt. Any acid addition salt will do so long as it is physiologically acceptable, for example, inorganic salts such as the hydrochloride, hydrobromide, sulphate, phosphate or the like or organic salts such as the acetate, maleate, fumarate, succinate, tartrate, citrate, maleate, or the like.

The compounds of the present invention contain an asymmetric carbon (shown by * in the following formula).

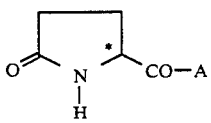

wherein A is as above defined.

According to the present invention, compounds of the formula Ib, DL-N-piperidinopyroglutamide, DL-N-pyrrolidinopyroglutamide and DL-N-morpholinopyroglutamide also contain an asymmetric carbon atom shown by the asterisk*

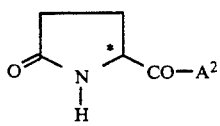

wherein $A^2$ is as below defined.

According to Japanese Laid Open Application 52/125166, production of the D-isomer contained some contamination of L-isomer even when a D-starting material is used. Therefore, it would be necessary to optically resolve the isomers, but such a method is not convenient or economical from an industrial standpoint. It has, therefore, been found that when the D-isomer of a compound of the formula IIIb

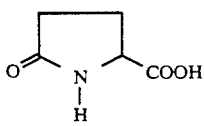

or a reactive derivative thereof is reacted with an amine of the formula $A^2$-H, wherein $A^2$ is unsubstituted pyrrolidino, piperidino, morpholino or thiomorpholino, only the corresponding D-isomers are obtained in high yield and high optical purity. It was also found that, quite unexpectedly, the D-isomer produced therefrom exhibits excellent nootropic action. When compound IIIb is reacted with an amine, this amidation reaction may be carried out in the following manner. The reaction may take place with various amines directly in the presence of DCC or DDPA; reactive derivatives of IIIb such as acid anhydrides, imidazolides or mixed acid anhydrides (acid anhydride with methyl carbonate, acid anhydride with ethyl carbonate, acid anhydride with isobutyl carbonate, etc.) are reacted. Among these methods, when condensation agents such as DCC are used, the reaction is conducted, for example, in a suitable solvent, for example a halogenated hydrocarbon such as methylene chloride, chloroform, etc.; ether type solvents such as tetrahydrofuran, dioxane, etc.; acetonitrile; N,N-dimethylformamide; etc. at about −30° C. to about 30° C. It is preferred to use equimolar or a little excess of the compound IIIb to one mole of amine when DCC is used.

The compounds may also be manufactured by the reaction of compound IIb with an amine of the formula $A^2$-H wherein $A^2$ is as above defined.

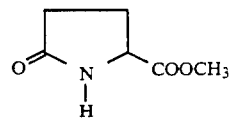

This amidation reaction may be conducted according to procedures per se known. Thus, for example, not less than equimolar (preferably 1.0-1.3 molar) amine to compound IIb is used and the reaction is carried out at room temperature (20° to 30° C.).

As to the solvent in that case, any inert solvent may be used, for example, alcohol type solvents (such as methanol, ethanol, isopropanol, etc.), halogenated hydrocarbon solvent (such as chloroform, carbon tetrachloride, etc.) aromatic hydrocarbon solvent (such as benzene, toluene, xylene, etc.), ether type solvent (such as tetrahydrofuran, dioxane, etc.) or aprotic and polar solvent (such as N,N-dimethylforamide) may be used. It is also acceptable that no solvent is used.

The compounds IIb and IIIb used as materials in the above manufacture methods may be easily manufactured by known methods. Similarly, the amines are available commercially or may be manufactured by known methods.

When racemic compounds (DL-compounds) are used as a starting material, the final compound is obtained as a mixture of D- and L-isomers which may be separated and the D-isomer is obtained in pure form by a conventional optical resolution.

The compound obtained by the above methods may be separated and purified by a methods known per se such as, for example, concentration, conversion of liquid property, dissolution into another phase, extraction using a solvent, crystallization, recrystallization, fractional distillation, chromatography, and the like.

Accordingly, there are optically-active D- and L-isomers and each optical isomer and mixture thereof are included as part of the present invention.

Those isomers may, if desired, be manufactured separately. For example, when an optically active compound (D- or L-) is used as a starting material in compounds II or III, the corresponding optically active isomer (D- or L-isomer) of compound I is produced. When the final compound I is a mixture of D- and L-isomers, it can be separated into each isomer by conventional optical resolution.

With respect to the optically active isomers of compounds of the formula I, it is the D-isomer which has better activity than the corresponding L-isomer.

The present invention includes pharmaceutical compositions containing 0.1 to 99.5%, more particularly, 0.5 to 90% of a compound of the formula I or a pharmaceutically acceptable acid additional salt thereof in combination with a pharmaceutically acceptable carrier. These compositions can be formulated by procedures known in the art.

Oral administration can be effected utilizing solid and liquid dosage unit forms such as powders, tablets, capsules granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatine sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicant when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acceptable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a give quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected by utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

While the dosage to be administered is based on the usual conditions such as the physical condition of the patient, age, body weight, past medical history, route of administrations, severity of the condition and the like, it is generally preferred to orally administer to a human 1 mg to 5 g per day and more preferably 150 mg to 3 g per day until amelioration of the condition occurs. The dose may be divided if desirable and given during the course of each day.

The following non-limitative Examples illustrate the preparation of the compounds of the present invention.

EXAMPLE 1 (METHOD A)

4-Benzyl-N-(2-pyrrolidone-5-carbonyl)-piperidine

Methyl pyroglutamate (4.3 g) and 7.9 g of 4-benzylpiperidine were dissolved in 20 ml of toluene and the mixture was heated to reflux with stirring for 24 hours. The reaction solution was treated with a silica gel column chromatography to give 7.2 g of the product which was recrystallized from diethyl ether to afford 6.5 g of desired product, m.p. 160°–161° C.

Elem. Anal. ($C_{17}H_{22}N_2O_2$) Calcd (%): C, 71.30; H, 7.74; N, 9.78. Found (%): C, 71.50; H, 8.17; N, 9.71.

EXAMPLE 2 (METHOD B)

1-(2-Pyrrolidone-5-carbonyl)piperazine

Pyroglutamic acid (112.4 g), 147.7 g of N-carbobenzoxypiperazine, 179.7 g of dicyclohexylcarbodiimide and 6.7 liters of acetonitrile were heated to reflux for 6 hours with stirring. The insoluble matters were removed by filtering the reaction mixture and the solvent was evaporated from the filtrate in vacuo. The residue was subjected to a silica gel column chromatography to give 190 g of oily N-carbobenzoxy-N'-(2-pyrrolidon-5-carbonyl)piperazine. Thirty grams of this was dissolved in 450 ml of methanol and the solution was subjected to a catalytic reduction using 3.0 g of 5% palladium-carbon with stirring at room temperature. The catalyst was removed by filtering the reaction solution and the solvent was evaporated in vacuo from the filtrate to give 20 g of the product. This was recrystallized from a mixture of methanol and ethyl acetate to give 17.5 g of desired compound, m.p. 162°–163° C.

Elem. Anal. ($C_9H_{15}N_3O_2$) Calcd (%): C, 54.81; H, 7.67; N, 21.30. Found (%): C, 54.74; H, 7.73; N, 21.29.

EXAMPLE 3 (METHOD B)

4-Morpholinocarbonylmethyl-1-(2-pyrrolidone-5-carbonyl)piperazine

Pyroglutamic acid (1.6 g), 2.1 g of 1-(morpholinocarbonylmethyl)piperazine, 2.47 g of DCC and 130 ml of acetonitrile were heated to reflux for 48 hours with stirring. The insoluble matter was removed by filtering the reaction mixture and the solvent was evaporated from the filtrate in vacuo. The residue was subjected to a silica gel column chromatography to give 3.0 g of the product. This was recrystallized from a mixture of ethyl acetate, isopropanol and n-hexane to give 2.6 g of desired product, m.p. 167°–169° C.

Elem. Anal. ($C_{15}H_{24}N_4O_4$) Calcd (%): C, 55.54; H, 7.46; N, 17.27. Found (%): C, 55.31; H, 7.49; N, 17.14.

EXAMPLE 4 (METHOD C)

4-Morpholinocarbonylmethyl-1-(2-pyrrolidone-5-carbonyl)piperazine 1-(2-Pyrrolidone-5-carbonyl)piperazine (3.7 g), 3.7 g of 4-chloroacetylmorpholine, 4.4 g of anhydrous potassium carbonate, and 20 ml of N,N-dimethylformamide were stirred at 70°–75° C. for 1 hour. The insoluble matter was removed by filtering the reaction mixture, the solvent was removed by evaporating the filtrate, and the residue was purified by a silica gel column chromatography to give 5.7 g of the product. This was recrystallized from a mixture of ethanol, ethyl acetate and diethyl ether to give 4.2 g of desired product, m.p. 167°–169° C.

Elem. Anal. ($C_{15}H_{24}N_4O_4$) Calcd (%): C, 55.54; H, 7.46; N, 17.27. Found (%): C, 55.36; H, 7.58; N, 17.23.

EXAMPLE 5 (METHOD D)

4-Ethoxycarbonyl-1-(2-pyrrolidone-5-carbonyl)piperazine

A mixed solution of 2.1 g of 1-(2-pyrrolidone-5-carbonyl)piperazine, 2.5 g of anhydrous potassium carbonate and 120 ml of acetonitrile was cooled with ice water and 1.1 g of ethyl chlorocarbonate in 10 ml of acetonitrile was dropped therein with stirring. After dropping, the mixture was stirred overnight at room temperature. The solvent was evaporated from the reaction mixture in vacuo, methylene chloride was added to the residue, and insoluble matter was removed therefrom by filtration. The solvent was evaporated in vacuo from the filtrate to give 2.3 g of oily product. This was crystallized from ethyl acetate and further recrystallized to give 2.1 g of desired product, m.p. 147°–148.5° C.

Elem. Anal. ($C_{12}H_{19}N_3O_4$) Calcd (%): C, 53.52; H, 7.11; N, 15.60. Found (%): C, 53.36; H, 7.32; N, 15.60.

EXAMPLE 6 (METHOD E)

4-Morpholinoacetyl-1-(2-pyrrolidone-5-carbonyl)piperazine

A mixed solution of 2.3 g of N-(2-pyrrolidone-5-carbonyl)piperazine, 50 ml of methylene chloride, and 2.8 g of anhydrous potassium carbonate was cooled with ice water and 1.3 g of chloro acetyl chloride was dropped therein with stirring. After the dropping, the mixture was stirred for another 1 hour at room temperature. The insoluble matter was removed by filtration and the solvent was evaporated in vacuo from the filtrate to give 2.3 g of oily N-(2-pyrrolidone-5-carbonyl)-N'-chloroacetylpiperazine. This was dissolved in 15 ml of N,N-dimethylformamide and 0.8 g of morpholine and 2.2 g of anhydrous potassium carbonate were added thereto, and the mixture was heated at 80° C. for 3 hours with stirring. The insoluble matter was filtered off therefrom and the solvent was evaporated in vacuo from the filtrate. The residue was purified by a silica gel column chromatography to give 2.5 g of the product. This was recrystallized from a mixture of methanol and ethyl ether to give 2.1 g of desired product, m.p. 204°–205° C.

Elem. Anal. ($C_{15}H_{24}N_4O_4$) Calcd (%): C, 55.54; H, 7.46; N, 17.27. Found (%): C, 55.23; H, 7.87; N, 17.01.

The compounds of Examples 7 to 107 were prepared in accordance with the methods given in Examples 1 to 6.

EXAMPLE 7

4-Phenyl-1-(2-pyrrolidone-5-carbonyl)piperazine, m.p. 201°–202° C.

Elem. Anal. ($C_{15}H_{19}N_3O_2$) Calcd (%): C, 65.91; H, 7.01; N, 15.37. Found (%): C, 65.93; H, 7.08; N, 15.12.

EXAMPLE 8

4-Benzhydryl-1-(2-pyrrolidone-5-carbonyl)piperazine, m.p. 147°–148.5° C.

Elem. Anal. ($C_{22}H_{25}N_3O_2$) Calcd (%): C, 72.70; H, 6.93; N, 11.56. Found (%): C, 72.53; H, 7.06; N, 11.32.

EXAMPLE 9

4-(2-Chlorophenyl)-1-(2-pyrrolidone-5-carbonyl)piperazine, m.p. 185.5°–186.5° C.

Elem. Anal. ($C_{15}H_{18}ClN_3O_2$) Calcd (%): C, 58.54; H, 5.89; N, 13.65. Found (%): C, 58.51; H, 5.92; N, 13.77.

EXAMPLE 10

4-(2-Chlorophenyl)-1-(2-pyrrolidone-5-carbonyl)piperazine, m.p. 165°–167° C.

Elem. Anal. ($C_{15}H_{18}ClN_3O_2$) Calcd (%): C, 58.54; H, 5.89; N, 13.65. Found (%): C, 58.41; H, 6.01; N, 13.60.

EXAMPLE 11

4-(4-Chlorophenyl)-1-(2-pyrrolidone-5-carbonyl)piperazine, m.p. 244.5°–246.5° C.

Elem. Anal. ($C_{15}H_{18}ClN_3O_2$) Calcd (%): C, 58.54; H, 5.89; N, 13.65. Found (%): C, 58.57; H, 5.92; N, 13.67.

EXAMPLE 12

4-(4-Fluorophenyl)-1-(2-pyrrolidone-5-carbonyl)piperazine, m.p. 212°–213.5° C.

Elem. Anal. ($C_{15}H_{18}FN_3O_2$) Calcd (%): C, 61.84; H, 6.23; N, 14.42. Found (%): C, 61.77; H, 6.34; N, 14.38.

EXAMPLE 13

4-(2-Methylphenyl)-1-(2-pyrrolidone-5-carbonyl)piperazine, m.p. 212°–213° C.

Elem. Anal. ($C_{16}H_{21}N_3O_2$) Calcd (%): C, 66.87; H, 7.37; N, 14.62. Found (%): C, 66.70; H, 7.50; N, 14.70.

EXAMPLE 14

L-(−)-4-(2-Methylphenyl)-1-(2-pyrrolidone-5-carbonyl)piperazine, m.p. 122°–123.5° C.

Elem. Anal. ($C_{16}H_{21}N_3O_2$) Calcd (%): C, 66.87; H, 7.37; N, 14.62. Found (%): C, 66.79; H, 7.60; N, 14.55.

EXAMPLE 15

1-(2-Pyrrolidone-5-carbonyl)-4-(3-trifluoromethylphenyl)piperazine, m.p. 133.5°–134.5° C.

Elem. Anal. ($C_{16}H_{18}F_3N_3O_2$) Calcd (%): C, 56.30; H, 5.32; N, 12.31. Found (%): C, 56.59; H, 5.41; N, 12.41.

EXAMPLE 16

4-(2-Methoxyphenyl)-1-(2-pyrrolidone-5-carbonyl)piperazine, m.p. 157°–158° C.

Elem. Anal. ($C_{16}H_{21}N_3O_3$) Calcd (%): C, 63.35; H, 6.98; N, 13.85. Found (%): C, 63.25; H, 7.07; N, 13.87.

EXAMPLE 17

4-(4-Methoxyphenyl)-1-(2-pyrrolidone-5-carbonyl)piperazine, m.p. 190°–192° C.

Elem. Anal. (C$_{16}$H$_{21}$N$_3$O$_3$) Calcd (%): C, 63.35; H, 6.98; N, 13.85. Found (%): C, 63.19; H, 7.22; N, 13.76.

EXAMPLE 18

4-(4-Acetylphenyl)-1-(2-pyrrolidone-5-carbonyl)piperazine, m.p. 227.5°–229.0° C.
Elem. Anal. (C$_{17}$H$_{21}$N$_3$O$_3$) Calcd (%): C, 64.74; H, 6.71; N, 13.32. Found (%): C, 64.65; H, 6.84; N, 13.30.

EXAMPLE 19

4-Benzyl-1-(2-pyrrolidone-5-carbonyl)piperazine, m.p. 139.5°–141.5° C.
Elem. Anal. (C$_{16}$H$_{21}$N$_3$O$_2$) Calcd (%): C, 66.88; H, 7.37; N, 14.62. Found (%): C, 66.60; H, 7.56; N, 14.60.

EXAMPLE 20

4-(2-Chlorobenzyl)-1-(2-pyrrolidone-5-carbonyl)piperazine, m.p. 92.5°–93.5° C.
Elem. Anal. (C$_{16}$H$_{20}$ClN$_3$O$_2$) Calcd (%): C, 59.72; H, 6.26; N, 13.06. Found (%): C, 59.72; H, 6.32; N, 13.17.

EXAMPLE 21

4-(4-Chlorobenzyl)-1-(2-pyrrolidone-5-carbonyl)piperazine, m.p. 163°–165° C.
Elem. Anal. (C$_{16}$H$_{20}$ClN$_3$O$_2$) Calcd (%): C, 59.72; H, 6.26; N, 13.06. Found (%): C, 59.44; H, 6.39; N, 12.80.

EXAMPLE 22

4-(4-Fluorobenzyl)-1-(2-pyrrolidone-5-carbonyl)piperazine, m.p. 142°–143° C.
Elem. Anal. (C$_{16}$H$_{20}$FN$_3$O$_2$) Calcd (%): C, 62.94; H, 6.60; N, 13.76. Found (%): C, 62.81; H, 6.79; N, 13.57.

EXAMPLE 23

4-(4-Methylbenzyl)-1-(2-pyrrolidone-5-carbonyl)piperazine, m.p. 144.5°–145.5° C.
Elem. Anal. (C$_{17}$H$_{23}$N$_3$O$_2$) Calcd (%): C, 67.75; H, 7.69; N, 13.94. Found (%): C, 67.71; H, 7.88; N, 13.94.

EXAMPLE 24

1-(2-Pyrrolidone-5-carbonyl)-4-(2-trifluoromethylbenzyl)piperazine hemifumarate, m.p. 133.5°–135.5° C.
Elem. Anal. (C$_{17}$H$_{20}$F$_3$N$_3$O$_2$·½C$_4$H$_4$O$_4$) Calcd (%) C, 55.20; H, 5.36; N, 10.16. Found (%): C, 55.06; H, 5.38; N, 10.12.

EXAMPLE 25

4-(4-Methoxybenzyl)-1-(2-pyrrolidone-5-carbonyl)piperazine, m.p. 145°–147° C.
Elem. Anal. (C$_{17}$H$_{23}$N$_3$O$_3$) Calcd (%): C, 64.33; H, 7.30; N, 13.24. Found (%): C, 64.29; H, 7.68; N, 13.21.

EXAMPLE 26

4-(3,4-Methylenedioxybenzyl)-1-(2-pyrrolidone-5-carbonyl)piperazine, m.p. 109°–111° C.
Elem. Anal. (C$_{17}$H$_{21}$N$_3$O$_4$) Calcd (%): C, 61.62; H, 6.39; N, 12.68. Found (%): C, 61.67; H, 6.55; N, 12.63.

EXAMPLE 27

4-Benzoyl-1-(2-pyrrolidone-5-carbonyl)piperazine, m.p. 173°–174° C.
Elem. Anal. (C$_{16}$H$_{19}$N$_3$O$_3$) Calcd (%): C, 63.77; H, 6.35; N, 13.94. Found (%): C, 63.59; H, 6.49; N, 13.98.

EXAMPLE 28

L-(−)-4-Benzoyl-1-(2-pyrrolidone-5-carbonyl)piperazine, m.p. 113.5°–115.5° C.
Elem. Anal. (C$_{16}$H$_{19}$N$_3$O$_3$) Calcd (%): C, 63.77; H, 6.35; N, 13.94. Found (%): C, 63.70; H, 6.82; N, 13.95.

EXAMPLE 29

4-(2-Methylbenzoyl)-1-(2-pyrrolidone-5-carbonyl)piperazine, m.p. 206°–207° C.
Elem. Anal. (C$_{17}$H$_{21}$N$_3$O$_3$) Calcd (%): C, 64.74; H, 6.71; N, 13.32. Found (%): C, 64.49; H, 6.94; N, 13.09.

EXAMPLE 30

4-(3-Methylbenzoyl)-1-(2-pyrrolidone-5-carbonyl)piperazine, m.p. 175°–176.5° C.
Elem. Anal. (C$_{17}$H$_{21}$N$_3$O$_3$) Calcd (%): C, 64.74; H, 6.71; N, 13.32. Found (%): C, 64.49; H, 6.94; N, 13.09.

EXAMPLE 31

4-(4-Methylbenzoyl)-1-(2-pyrrolidone-5-carbonyl)piperazine, m.p. 162°–164° C.
Elem. Anal. (C$_{17}$H$_{21}$N$_3$O$_3$) Calcd (%): C, 64.74; H, 6.71; N, 13.32. Found (%): C, 64.41; H, 6.80; N, 13.24.

EXAMPLE 32

4-(2,4-Dimethylbenzoyl)-1-(2-pyrrolidone-5-carbony)piperazine, m.p. 213°–215° C.
Elem. Anal. (C$_{18}$H$_{23}$N$_3$O$_3$) Calcd (%): C, 65.63; H, 7.04; N, 12.76. Found (%): C, 65.57; H, 7.26; N, 12.77.

EXAMPLE 33

4-(4-Methoxybenzoyl)-1-(2-pyrrolidone-5-carbonyl)piperazine, m.p. 180.5°–182.5° C.
Elem. Anal. (C$_{17}$H$_{21}$N$_3$O$_4$) Calcd (%): C, 61.61; H, 6.39; N, 12.68. Found (%): C, 61.70; H, 6.56; N, 12.72.

EXAMPLE 34

1-(2-Pyrrolidone-5-carbonyl)-4-(3,4,5-trimethoxybenzoyl)piperazine, m.p. 170°–172° C.
Elem. Anal. (C$_{19}$H$_{25}$N$_3$O$_6$) Calcd (%): C, 58.30; H, 6.44; N, 10.74. Found (%): C, 58.27; H, 6.59; N, 10.75.

EXAMPLE 35

4-(4-Nitrobenzoyl)-1-(2-pyrrolidone-5-carbonyl)piperazine, m.p. 205.5°–207.5° C.
Elem. Anal. (C$_{16}$H$_{18}$N$_4$O$_5$) Calcd (%): C, 55.49; H, 5.24; N, 16.18. Found (%): C, 55.33; H, 5.34; N, 16.23.

EXAMPLE 36

4-(4-Fluorobenzoyl)-1-(2-pyrrolidone-5-carbonyl)piperazine, m.p. 195.5°–197.5° C. (decomposition).
Elem. Anal. (C$_{16}$H$_{18}$FN$_3$O$_3$) Calcd (%): C, 60.18; H, 5.68; N, 13.16. Found (%): C, 60.20; H, 5.71; N, 13.20.

EXAMPLE 37

4-(2-Chlorobenzoyl)-1-(2-pyrrolidone-5-carbonyl)piperazine, m.p. 175°–177° C.
Elem. Anal. (C$_{16}$H$_{18}$ClN$_3$O$_3$) Calcd (%): C, 57.23; H, 5.40; N, 12.51. Found (%): C, 57.21; H, 5.46; N, 12.43.

EXAMPLE 38

4-(4-Chlorobenzoyl)-1-(2-pyrrolidone-5-carbonyl)piperazine, m.p. 179°–181° C.
Elem. Anal. (C$_{16}$H$_{18}$ClN$_3$O$_3$) Calcd (%): C, 57.23; H, 5.40; N, 12.51. Found (%): C, 56.94; H, 5.54; N, 12.45.

EXAMPLE 39

4-(2,4-Dichlorobenzoyl)-1-(2-pyrrolidone-5-carbony)piperazine, m.p. 206°–208° C.

Elem. Anal. ($C_{16}H_{17}Cl_2N_3O_3$) Calcd (%): C, 51.91; H, 4.63; N, 11.35. Found (%): C, 52.00; H, 4.63; N, 11.31.

EXAMPLE 40

4-Phenylacetyl-1-(2-pyrrolidone-5-carbonyl)piperazine, m.p. 150.5°–152.0° C.

Elem. Anal. ($C_{17}H_{21}N_3O_3$) Calcd (%): C, 64.74; H, 6.71; N, 13.32. Found (%): C, 64.37; H, 6.89; N, 13.28.

EXAMPLE 41

4-(4-Methoxyphenylacetyl)-1-(2-pyrrolidone-5-carbonyl)piperazine, m.p. 148.5°–149.5° C.

Elem. Anal. ($C_{18}H_{23}N_3O_4$) Calcd (%): C, 62.59; H, 6.71; N, 12.17. Found (%): C, 62.55; H, 6.90; N, 12.22.

EXAMPLE 42

4-(4-Chlorophenylacetyl)-1-(2-pyrrolidone-5-carbonyl)piperazine, m.p. 185°–187° C.

Elem. Anal. ($C_{17}H_{20}ClN_3O_3$) Calcd (%): C, 58.37; H, 5.76; N, 12.01. Found (%): C, 58.50; H, 5.84; N, 12.09.

EXAMPLE 43

4-Methyl-1-(2-pyrrolidone-5-carbonyl)piperazine, m.p. 129°–131° C.

Elem. Anal. ($C_{10}H_{17}N_3O_2$) Calcd (%): C, 56.85; H, 8.11; N, 19.89. Found (%): C, 56.85; H, 7.96; N, 19.37.

EXAMPLE 44

4-Acetyl-1-(2-pyrrolidone-5-carbonyl)piperazine, m.p. 118°–123° C.

Elem. Anal. ($C_{11}H_{17}N_3O_3 \cdot 1/6H_2O$) Calcd (%): C, 54.53; H, 7.21; N, 17.34. Found (%): C, 54.55; H, 7.82; N, 17.37.

EXAMPLE 45

4-Propanoyl-1-(2-pyrrolidone-5-carbonyl)piperazine, m.p. 138°–139° C.

Elem. Anal. ($C_{12}H_{19}N_3O_3$) Calcd (%): C, 56.90; H, 7.56; N, 16.59. Found (%): C, 56.76; H, 7.78; N, 16.53.

EXAMPLE 46

4-Carbobenzoxy-1-(2-pyrrolidone-5-carbonyl)piperazine, m.p. 162°–164° C.

Elem. Anal. ($C_{17}H_{21}N_3O_4$) Calcd (%): C, 61.62; H, 6.39; N, 12.68. Found (%): C, 61.46; H, 6.46; N, 12.56.

EXAMPLE 47

4-Cinnamoyl-1-(2-pyrrolidone-5-carbonyl)piperazine, m.p. 229°–233° C. (decomposition).

Elem. Anal. ($C_{18}H_{21}N_3O_3$) Calcd (%): C, 66.04; H, 6.47; N, 12.84. Found (%): C, 65.83; H, 6.61; N, 13.12.

EXAMPLE 48

4-(4-Methylcinnamoyl)-1-(2-pyrrolidone-5-carbonyl)piperazine, m.p. 253.5°–255.5° C. (decomposition).

Elem. Anal. ($C_{19}H_{23}N_3O_3$) Calcd (%): C, 66.84; H, 6.79; N, 12.31. Found (%): C, 66.73; H, 6.91; N, 12.26.

EXAMPLE 49

4-(4-Methoxycinnamoyl)-1-(2-pyrrolidone-5-carbonyl)piperazine, m.p. 204°–231° C.

Elem. Anal. ($C_{19}H_{23}N_3O_4$) Calcd (%): C, 63.85; H, 6.49; N, 11.76. Found (%): C, 63.94; H, 6.59; N, 11.76.

EXAMPLE 50

4-(N,N-Dimethylcarbamoyl)-1-(2-pyrrolidone-5-carbonyl)piperazine, m.p. 178.5°–179.5° C.

Elem. Anal. ($C_{12}H_{20}N_4O_3$) Calcd (%): C, 53.72; H, 7.51; N, 20.88. Found (%): C, 53.61; H, 7.79; N, 20.71.

EXAMPLE 51

4-Isopropylaminocarbonylmethyl-1-(2-pyrrolidone-5-carbonyl)piperazine, m.p. 125°–127° C.

Elem. Anal. ($C_{14}H_{24}N_4O_3$) Calcd (%): C, 56.74; H, 8.16; N, 18.90. Found (%): C, 56.54; H, 8.43; N, 18.76.

EXAMPLE 52

4-Nicotinoyl-1-(2-pyrrolidone-5-carbonyl)piperazine, m.p. 199.5°–201.5° C.

Elem. Anal. ($C_{15}H_{18}N_4O_3$) Calcd (%): C, 59.59; H, 6.00; N, 18.53. Found (%): C, 59.31; H, 6.01; N, 18.32.

EXAMPLE 53

1-(2-Pyrrolidone-5-carbonyl)-4-(2-thienoyl)piperazine, m.p. 170.5°–172.5° C.

Elem. Anal. ($C_{14}H_{17}N_3O_3S$) Calcd (%): C, 54.71; H, 5.57; N, 13.67. Found (%): C, 54.62; H, 5.56; N, 13.80.

EXAMPLE 54

4-(2-Pyridyl)-1-(2-pyrrolidone-5-carbonyl)piperazine, m.p. 211°–212.5° C.

Elem. Anal. ($C_{14}H_{18}N_4O_2$) Calcd (%): C, 61.30; H, 6.61; N, 20.42. Found (%): C, 61.25; H, 6.73; N, 20.38.

EXAMPLE 55

4-Methyl-N-(2-pyrrolidone-5-carbonyl)piperidine, m.p. 107°–109° C.

Elem. Anal. ($C_{11}H_{18}N_2O_2$) Calcd (%): C, 62.83; H, 8.63; N, 13.32. Found (%): C, 62.40; H, 8.90; N, 13.17.

EXAMPLE 56

4-Phenyl-N-(2-pyrrolidone-5-carbonyl)piperidine, m.p. 198°–199° C.

Elem. Anal. ($C_{16}H_{20}N_2O_2$) Calcd (%): C, 70.56; H, 7.40; N, 10.29. Found (%): C, 70.68; H, 7.66; N, 10.15.

EXAMPLE 57

4-Ethoxycarbonyl-N-(2-pyrrolidone-5-carbonyl)piperidine, m.p. 158.0°–159.5° C.

Elem. Anal. ($C_{13}H_{20}N_2O_4$) Calcd (%): C, 58.19; H, 7.51; N, 10.44. Found (%): C, 58.18; H, 7.82; N, 10.44.

EXAMPLE 58

4-Carbamoyl-N-(2-pyrrolidone-5-carbonyl)piperidine hemihydrate, m.p. 172°–173° C.

Elem. Anal. ($C_{11}H_{17}N_3O_3 \cdot \frac{1}{2}H_2O$) Calcd (%): C, 53.22; H, 7.31; N, 16.92. Found (%): C, 53.67; H, 7.79; N, 16.76.

EXAMPLE 59

4-Hydroxy-N-(2-pyrrolidone-5-carbonyl)piperidine, m.p. 147.0°–148.5° C.

Elem. Anal. ($C_{10}H_{16}N_2O_3$) Calcd (%): C, 56.59; H, 7.60; N, 13.20. Found (%): C, 56.71; H, 7.94; N, 13.12.

EXAMPLE 60

N-(2-Pyrrolidone-5-carbonyl)hexamethyleneimine, m.p. 87°–89° C.

Elem. Anal. ($C_{11}H_{18}N_2O_2$) Calcd (%): C, 62.83; H, 8.63; N, 13.32. Found (%): C, 62.84; H, 8.92; N, 13.39.

EXAMPLE 61

4-(2-Pyrrolidone-5-carbonyl)-2-ketopiperazine, m.p. 198°–200° C.

Elem. Anal. ($C_9H_{13}N_3O_3$) Calcd (%): C, 51.28; H, 6.20; N, 19.89. Found (%): C, 51.21; H, 6.20; N, 19.80.

EXAMPLE 62

L-(−)-4-(Morpholinocarbonylmethyl)-1-(2-pyrrolidone-5-carbonyl)piperazine maleate, m.p. 201°–202.5° C.

Elem. Anal. ($C_{15}H_{14}N_4O_4C_4H_4O_4$) Calcd (%): C, 51.81; H, 6.41; N, 12.72. Found (%): C, 51.61; H, 6.67; N, 12.73.

EXAMPLE 63

4-Pyrrolidinocarbonylmethyl-1-(2-pyrrolidone-5-carbonyl)piperazine, m.p. 179°–180° C.

Elem. Anal. ($C_{15}H_{24}N_4O_3$) Calcd (%): C, 58.42; H, 7.84; N, 18.17. Found (%): C, 58.26; H, 8.02; N, 18.06.

EXAMPLE 64

4-Piperidinocarbonylmethyl-1-(2-pyrrolidone-5-carbonyl)piperazine, m.p. 181°–183° C.

Elem. Anal. ($C_{16}H_{26}N_4O_3$) Calcd (%): C, 59.61; H, 8.13; N, 17.38. Found (%): C, 59.46; H, 8.48; N, 17.23.

EXAMPLE 65

4-Hexyliminocarbonylmethyl-1-(2-pyrrolidone-5-carbonyl)piperazine, m.p. 143°–144° C.

Elem. Anal. ($C_{17}H_{28}N_4O_3$) Calcd (%): C, 60.69; H, 8.39; N, 16.65. Found (%): C, 60.42; H, 8.45; N, 16.45.

EXAMPLE 66

4-Diisopropylaminocarbonylmethyl-1-(2-pyrrolidone-5-carbonyl)piperazine, m.p. 189°–190.5° C.

Elem. Anal. ($C_{17}H_{30}N_4O_3$) Calcd (%): C, 60.33; H, 8.93; N, 16.55. Found (%): C, 60.03; H, 9.24; N, 16.55.

EXAMPLE 67

4-Morpholinoethyl-1-(2-pyrrolidone-5-carbonyl)piperazine maleate, m.p. 179°–181° C.

Elem. Anal. ($C_{15}H_{26}N_4O_3.2C_4H_4O_4.\frac{1}{2}H_2O$) Calcd (%): C, 50.09; H, 6.40; N, 10.16. Found (%): C, 49.99; H, 6.74; N, 10.22.

EXAMPLE 68

4-Pyrrolidinoethyl-1-(2-pyrrolidone-5-carbonyl)piperazine maleate, m.p. 169°–170° C.

Elem. Anal. ($C_{15}H_{26}N_4O_2.2C_4H_4O_4.\frac{1}{2}H_2O$) Calcd (%): C, 51.58; H, 6.59; N, 10.46. Found (%): C, 51.60; H, 6.90; N, 10.29.

EXAMPLE 69

4-Piperidinoethyl-1-(2-pyrrolidone-5-carbonyl)piperazine, m.p. 131°–133° C.

Elem. Anal. ($C_{16}H_{28}N_4O_2$) Calcd (%): C, 62.31; H, 9.15; N, 18.17. Found (%): C, 61.83; H, 9.16; N, 18.08.

EXAMPLE 70

4-Pyrrolidinoacetyl-1-(2-pyrrolidone-5-carbonyl)piperazine, m.p. 166.5°–168.0° C.

Elem. Anal. ($C_{15}H_{24}N_4O_3$) Calcd (%): C, 57.58; H, 7.89; N, 17.91. Found (%): C, 57.55; H, 8.04; N, 17.99.

EXAMPLE 71

4-Piperidinoacetyl-1-(2-pyrrolidone-5-carbonyl)piperazine, m.p. 195°–196° C.

Elem. Anal. ($C_{19}H_{26}N_4O_3$) Calcd (%): C, 59.61; H, 8.13; N, 17.38. Found (%): C, 59.16; H, 8.42; N, 17.43.

EXAMPLE 72

D-(+)-4-Morpholinocarbonylmethyl-1-(2-pyrrolidone-5-carbonyl)piperazine maleate, m.p. 199°–201° C.

Elem. Anal. ($C_{15}H_{24}N_4O_4.C_4H_4O_4$) Calcd (%): C, 51.81; H, 6.41; N, 12.72. Found (%): C, 51.75; H, 6.29; N, 12.76.

EXAMPLE 73

D-(+)-4-Ethoxycarbonyl-1-(2-pyrrolidone-5-carbonyl)piperazine, m.p. 71°–73° C.

Elem. Anal. ($C_{12}H_{19}N_3O_4.\frac{1}{4}H_2O$) Calcd (%): C, 52.64; H, 7.18; N, 15.35. Found (%): C, 52.69; H, 7.26; N, 15.46.

EXAMPLE 74

D-(+)-4-Morpholinoacetyl-1-(2-pyrrolidone-5-carbonyl)piperazine, m.p. 139°–141° C.

Elem. Anal. ($C_{15}H_{24}N_4O_4.\frac{1}{4}H_2O$) Calcd (%): C, 54.78; H, 7.51; N, 17.04. Found (%): C, 54.88; H, 7.66; N, 17.12.

EXAMPLE 75

4-(2-Phenoxyethyl)-1-(2-pyrrolidone-5-carbonyl)piperazine, m.p. 131.5°–133.0° C.

Elem. Anal. ($C_{17}H_{23}N_3O_3$) Calcd (%): C, 64.33; H, 7.30; N, 13.24. Found (%): C, 64.38; H, 7.28; N, 13.29.

EXAMPLE 76

4-[2-(4-Methylphenoxy)ethyl]-1-(2-pyrrolidone-5-carbonyl)piperazine, m.p. 146°–147.5° C.

Elem. Anal. ($C_{18}H_{25}N_3O_3$) Calcd (%): C, 65.24; H, 7.60; N, 12.68. Found (%): C, 65.26; H, 7.60; N, 12.70.

EXAMPLE 77

4-[2-(2-Chlorophenoxy)ethyl]-1-(2-pyrrolidone-5-carbonyl)piperazine, m.p. 133°–134° C.

Elem. Anal. ($C_{17}H_{22}ClN_3O_3$) Calcd (%): C, 58.04; H, 6.30; N, 11.94. Found (%): C, 57.95; H, 6.30; N, 11.90.

EXAMPLE 78

D-(+)-4-(4-Methylbenzyl)-1-(2-pyrrolidone-5-carbonyl)piperazine, m.p. 71°–73° C.

Elem. Anal. ($C_{17}H_{23}N_3O_2.H_2O$) Calcd (%): C, 63.93; H, 7.89; N, 13.16. Found (%): C, 63.88; H, 7.92; N, 13.25.

EXAMPLE 79

D-(−)-5-(2-Carbamoyl-L-pyrrolidinocarbonyl)-2-pyrrolidone, m.p. 210°–211.5° C.

Elem. Anal. ($C_{10}H_{15}N_3O_3$) Calcd (%): C, 53.32; H, 6.71; N, 18.66. Found (%): C, 53.40; H, 6.76; N, 18.74.

EXAMPLE 80

1-(2-Pyrrolidone-5-carbonyl)-4-thiomorpholinocarbonylmethylpiperazine, m.p. 194°–195° C.

Elem. Anal. ($C_{15}H_{24}N_4O_3S$) Calcd (%): C, 52.92; H, 7.11; N, 16.46. Found (%): C, 52.91; H, 7.10; N, 16.44.

EXAMPLE 81

4-(4-Methoxycarbonylbenzyl)-1-(2-pyrrolidone-5-carbonyl)piperazine, m.p. 113.5°–115.5° C.

Elem. Anal. ($C_{18}H_{23}N_3O_4$) Calcd (%): C, 62.59; H, 6.71; N, 12.17. Found (%): C, 62.37; H, 6.85; N, 12.15.

EXAMPLE 82

4-(2-Hydroxyethyl)-1-(2-pyrrolidone-5-carbonyl)piperazine, m.p. 129°–131° C.

Elem. Anal. ($C_{11}H_{19}N_3O_3$) Calcd (%): C, 54.76; H, 7.94; N, 17.41. Found (%): C, 54.67; H, 8.06; N, 17.48.

EXAMPLE 83

4-(2-Morpholinocarbonylethyl)-1-(2-pyrrolidone-5-carbonyl)piperazine, m.p. 135°–136.5° C.

Elem. Anal. ($C_{16}H_{26}N_4O_4$) Calcd (%): C, 56.79; H, 7.74; N, 16.56. Found (%): C, 56.59; H, 7.89; N, 16.42.

EXAMPLE 84

4-(3-(4-Methylphenoxy)propyl)-1-(2-pyrrolidone-5-carbonyl)piperazine, m.p. 107°–108.5° C.

Elem. Anal. ($C_{19}H_{27}N_3O_3$) Calcd (%): C, 66.06; H, 7.88; N, 12.16. Found (%): C, 65.94; H, 7.96; N, 11.92.

EXAMPLE 85

4-[2-(4-Methoxycarbonylphenoxy)ethyl]-1-(2-pyrrolidone-5-carbonyl)piperazine, m.p. 127°–129° C.

Elem. Anal. ($C_{19}H_{25}N_3O_5$) Calcd (%): C, 60.79; H, 6.71; N, 11.19. Found (%): C, 60.62; H, 6.82; N, 11.02.

EXAMPLE 86

4-[3-(4-Methoxycarbonylphenoxy)propyl]-1-(2-pyrrolidone-5-carbonyl)piperazine, m.p. 141°–142.5° C.

Elem. Anal. ($C_{20}H_{27}N_3O_5$) Calcd (%): C, 61.68; H, 7.00; N, 10.79. Found (%): C, 61.60; H, 7.13; N, 10.71.

EXAMPLE 87

4-[2-(4-Benzyloxyphenoxy)ethyl]-1-(2-pyrrolidone-5-carbonyl)piperazine, m.p. 110°–112° C.

Elem. Anal. ($C_{24}H_{29}N_3O_4$.½$H_2O$) Calcd (%): C, 68.07; H, 6.90; N, 9.92. Found (%): C, 68.00; H, 7.00; N, 9.96.

EXAMPLE 88

4-(3-Morpholinopropionyl)-1-(2-pyrrolidone-5-carbonyl)piperazine, m.p. 184°–185° C.

Elem. Anal. ($C_{16}H_{26}N_4O_4$.½$H_2O$) Calcd (%): C, 55.32; H, 7.83; N, 16.13. Found (%): C, 55.65; H, 7.94; N, 16.08.

EXAMPLE 89

4-Morpholinocarbonylmethyl-1-(2-pyrrolidone-5-carbonyl)homopiperazine. Oily substance.

Elem. Anal. ($C_{16}H_{26}N_4O_4$) Calcd. (%): C, 56.79; H, 7.74; N, 16.56. Found (%): C, 56.83; H, 7.62; N, 16.57.

EXAMPLE 90

N-(2-Pyrrolidone-5-carbonyl)-1,2,3,4-tetrahydroisoquinoline. M.p. 153°–155° C.

Elem. Anal. ($C_{14}H_{16}N_2O_2$) Calcd (%): C, 68.83; H, 6.60; N, 11.47. Found (%): C, 68.96; H, 6.56; N, 11.53.

EXAMPLE 91

4-Acetamido-1-(2-pyrrolidone-5-carbonyl)piperidine M.p. 234.5°–236° C.

Elem. Anal. ($C_{12}H_{19}N_3O_3$) Calcd (%): C, 56.90; H, 7.56; N, 16.59. Found (%): C, 56.76; H, 7.74; N, 16.63.

EXAMPLE 92

4-(4-Benzyloxycarbonylpiperazinocarbonylmethyl)-1-(2-pyrrolidone-5-carbonyl)piperazine. M.p. 171°–174° C.

Elem. Anal. ($C_{23}H_{31}N_5O_5$) Calcd (%): C, 60.38; H, 6.83; N, 15.31. Found (%): C, 60.14; H, 7.12; N, 15.09.

EXAMPLE 93

4-Piperazinocarbonylmethyl-1-(2-pyrrolidone-5-carbonyl)piperazine maleate. M.p. 142°–144° C.

Elem. Anal. ($C_{15}H_{25}N_5O_3$.$C_8H_8O_8$.½$H_2O$) Calcd (%): C, 49.33; H, 5.98; N, 12.51. Found (%): C, 49.28; H, 5.99; N, 12.46.

EXAMPLE 94

4-[(4-Methylbenzyl)piperazinocarbonylmethyl]-1-(2-pyrrolidone-5-carbonyl)piperazine. M.p. 168°–170.5° C.

Elem. Anal. ($C_{23}H_{33}N_5O_3$) Calcd (%): C, 64.61; H, 7.78; N, 16.38. Found (%): C, 64.55; H, 7.87; N, 16.24.

EXAMPLE 95

4-[3-(4-Methylphenyl)propyl]-1-(2-pyrrolidone-5-carbonyl)piperazine. M.p. 74°–76° C.

Elem. Anal. ($C_{19}H_{27}N_3O_2$) Calcd (%): C, 69.27; H, 8.26; N, 12.75. Found (%): C, 69.31; H, 8.14; N, 12.76.

EXAMPLE 96

N-(2-Pyrrolidone-5-carbonyl)piperidine-4-one. M.p. 153°–155° C.

Elem. Anal. ($C_{10}H_{14}N_2O_3$) Calcd (%): C, 57.13; H, 6.71; N, 13.32. Found (%): C, 56.94; H, 6.61; N, 13.03.

EXAMPLE 97

D-(+)-4-Morpholinocarbonylmethyl-1-(2-pyrrolidone-5-carbonyl)piperazine. M.p. 129°–129.5° C.

Elem. Anal. ($C_{15}H_{24}N_4O_4$.½$C_2H_5OH$) Calcd (%): C, 55.32; H, 7.83; N, 16.13. Found (%): C, 55.48; H, 7.80; N, 16.26.

EXAMPLE 98

4-Benzyloxycarbonyl-1-(2-pyrrolidone-5-carbonyl)homopiperazine. M.p. 111°–113° C.

Elem. Anal. ($C_{18}H_{23}N_3O_4$) Calcd (%): C, 62.59; H, 6.71; N, 12.17. Found (%): C, 62.57; H, 6.75; N, 12.20.

EXAMPLE 99

4-Morpholinoacetyl-1-(2-pyrrolidone-5-carbonyl)homopiperazine fumarate. M.p. 148°–150° C.

Elem. Anal. ($C_{16}H_{26}N_4O_4$.$C_4H_4O_4$.½$H_2O$) Calcd (%): C, 52.34; H, 6.70; N, 12.21. Found (%): C, 52.26; H, 6.68; N, 11.99.

EXAMPLE 100

4-Morpholinocarbonyl-1-(2-pyrrolidone-5-carbonyl)piperazine. M.p. 183°–185° C.

Elem. Anal. ($C_{14}H_{22}N_4O_4$) Calcd (%): C, 54.18; H, 7.14; N, 18.05. Found (%): C, 54.07; H, 7.25; N, 17.76.

EXAMPLE 101

2-[4-(2-L-Carbamoylpyrrolidinocarbonylmethyl)piperazinocarbonyl]-D-pyrrolidin-5-one. M.p. 239°–242° C.

Elem. Anal. ($C_{16}H_{25}N_5O_4$.½$CH_3OH$) Calcd (%): C, 53.94; H, 7.41; N, 19.06. Found (%): C, 54.33; H, 7.41; N, 19.11.

EXAMPLE 102

4-Piperidino-1-(2-pyrrolidone-5-carbonyl)piperidine. M.p. 147°–150° C.

Elem. Anal. ($C_{15}H_{25}N_3O_2$) Calcd (%): C, 64.49; H, 9.02; N, 15.04. Found (%): C, 64.33; H, 8.98; N, 14.97.

EXAMPLE 103

D-(+)-4-Benzyloxycarbonyl-1-(2-pyrrolidone-5-carbonyl)piperazine. M.p. 49°–52° C.

Elem. Anal. ($C_{17}H_{21}N_3O_4$) Calcd (%): C, 61.46; H, 6.46; N, 12.56. Found (%): C, 61.30; H, 6.12; N, 12.63.

EXAMPLE 104

N-(2-Pyrrolidone-5-carbonyl)-2,6-cis-dimethylpiperidine. M.p. 177°–181° C.

Elem. Anal. ($C_{12}H_{20}N_2O_2$) Calcd (%): C, 64.26; H, 8.99; N, 12.49. Found (%): C, 64.11; H, 9.11; N, 12.47.

EXAMPLE 105

D-(+)-4-Thiomorpholinocarbonylmethyl-1-(2-pyrrolidone-5-carbonyl)piperazine maleate. M.p. 159°–161° C.

Elem. Anal. ($C_{15}H_{24}N_4O_3S \cdot C_4H_4O_4$) Calcd (%): C, 49.99; H, 6.18; N, 12.27. Found (%): C, 49.84; H, 6.20; N, 12.28.

EXAMPLE 106

1-(4-Aminobutanoyl)-4-(2-pyrrolidone-5-carbonyl)piperazine. M.p. 101°–102° C.

Elem. Anal. ($C_{13}H_{22}N_4O_3 \cdot \frac{1}{2}H_2O$) Calcd (%): C, 53.59; H, 7.96; N, 19.22. Found (%): C, 53.75; H, 7.73; N, 18.97.

EXAMPLE 107

1-[4-(N-Benzyloxycarbonylamino)butanoyl]-4-(2-pyrrolidone-5-carbonyl)piperazine. M.p. 157°–159.5° C.

Elem. Anal. ($C_{21}H_{28}N_4O_5$) Calcd (%): C, 60.56; H, 6.78; N, 13.45. Found (%): C, 60.58; H, 6.70; N, 13.42.

EXAMPLE 108

Synthesis of N-(5-oxo-D-prolyl) piperidine.

A solution comprising 45.0 g of D-pyroglutamic acid, 450 ml of acetonitrile, and 22.8 g of piperidine was cooled with ice water and 71.9 g of dicyclohexylcarbodiimide was added thereto at not higher than 10° C. with stirring. The mixture was reacted at room temperature for 5 hours more. Insoluble material was removed from the reaction mixture by filtration and the solvent was evaporated in vacuo from the filtrate.

The residue was subjected to a silica gel column chromatography to purify it and 60.0 g of oily product was obtained. This was crystallized from a mixed solvent of ethyl acetate and diethyl ether to give 44.7 g of N-(D-2-pyrrolidone-5-carbonyl) piperidine, m.p. 94.0°–95.0° C.

Optical rotation: $[\alpha]24/D + 48.32°$ (water, c=1)

Elementary analysis calculated as $C_{10}H_{16}N_2O_2$: Calcd: C:61.20, H:8.22, N:14.27; Found: C:61.16, H:8.17, N:14.30%

Using the procedures set forth in the above Example 108, the following compounds were also produced:
N-(5-oxo-D-prolyl) pyrrolidine;
N-(5-oxo-D-prolyl) morpholine; and
N-(5-oxo-D-prolyl) thiomorpholine.

The activity of the compounds of the invention may be seen from the following data:

Improving Effect on Memory Disruption Induced by Scopolamine

Test method: After acquiring a passive avoidance response (PAR) (acquisition session), 0.5 mg/kg of scopolamine and the test drug were simultaneously administered i.p. to rats and, after one hour, the passive avoidance response (retention test) was done again. The rate of positive reaction at that time (numbers of positive animals/numbers of used) is given in Table 1 below. In the above test, the retention test was done at 2 hours after oral administration of the drug.

Minimum effective dose showing significant improving effect by intraperitoneal and oral administration of aniracetam and the compounds of Examples 3 and 72 are shown in part (1) of Table 2 below.

TABLE 1

| Drug Used (Example Number) | Rate of Positive Reaction (positive animals/animals/used) Dose (mg/kg intraperitoneal) | | | | | |
|---|---|---|---|---|---|---|
| | 0.1 | 0.3 | 1 | 3 | 10 | 30 |
| Aniracetam | — | — | ⅛ | ⅛* | ⅛* | 4/8 |
| 3 | — | ⅛ | 4/8 | 6/8* | ⅛** | — |
| 5 | — | 2/8 | 6/8* | 4/8 | — | — |
| 23 | — | 2/8 | 6/8* | ⅛* | — | — |
| 72 | ⅛* | ⅛* | ⅛** | ⅛* | — | — |

*p < 0.05
**p < 0.01

It is apparent that the present invention compounds exhibit marked effects.

Improving Effect on Memory Disruption Induced by Electric Shock

The same method as that in the scopolamine-induced memory disruption was used.

After the acquisition session, rats were subjected to an electric shock and, after the recovery from convulsion, drug was administered intraperitoneally or orally. The retention session was conducted after 1 and 3 hours, respectively, the rate of positive reaction at that time was measured and minimum doses showing the significant improving effect are shown in (2) of Table 2.

Memory Disruption by an Excess of $CO_2$

The drug was given intraperitoneally or orally and after 30 and 60 minutes, respectively, rats were placed for 12 seconds in a chamber filled with $CO_2$ gas. After 3 minutes, they were moved to a two compartment shuttle box, subjected to an active avoidance response and escape response using a buzzer as conditioned stimulation, and the rate of positiveness (numbers of positive animals/numbers of all animals used) of response acquiring test after six trials was measured and minimum effective doses showing the significant improving effect are shown in (3) of Table 2. The minimum effective dose in Table 2 is given by as an effective amount (mg/kg) showing the significant improving effect by $p<0.05$ in $\chi^2$ assay.

TABLE 2

| Drug Used (Example Number) | Route of Administration | Minimum Effective Dose (mg/kg) | | |
|---|---|---|---|---|
| | | (1) | (2) | (3) |
| Aniracetam | i.p. | 3 | 30 | 30 |
| | p.o. | 50 | 50 | 50 |
| 3 | i.p. | 3 | 30 | 30 |
| | p.o. | 30 | 30 | 30 |
| 72 | i.p. | 0.1 | 10 | 3 |
| | p.o. | 3 | 10 | 10 |

It is apparent that the present invention exhibit marked activity.

Acute Toxicity.

Male mice were given the compounds of the present invention (examples 3 and 72) intravenously and orally and, after seven days, were observed for signs of toxicity.

When 1000 mg/kg was intravenously injected, no death was observed from either compound and essentially no toxic signs were observed.

In the case of oral administration, no death was observed after administration of 3000 mg/kg and no toxic signs were observed.

It is apparent that the compounds of the present invention are quite safe.

In addition, the following compounds were also tested by the above procedure: N-(2-pyrrolidone-5-carbonyl) piperidine (A in Tables 3 and 4), N-(2-pyrrolidone-5-carbonyl) pyrrolidine (B in Table 3) and N-(2-pyrrolidone-5-carbonyl) morpholine (C in Table 3). The minimum effective doses showing a significant improvement effect by intraperitoneal and oral administration are set forth in Table 3 and in part (1) of Table 4 below.

TABLE 3

| Drug Used | Rate of Positive Reaction (Pos Animals/All Animals) Dose (mg/kg. i.p.) | | | | |
|---|---|---|---|---|---|
| | 0.3 | 1 | 3 | 10 | 30 |
| Aniracetam | — | ⅛ | ⅛* | ⅛* | 4/8 |
| (A) DL-Compound | ⅛ | ⅛* | ⅛* | 8/8** | 4/8 |
| (A) D-Compound | ⅛* | 6/8** | ⅛ | — | — |
| (B) DL-Compound | — | — | 2/7 | 4/8 | — |
| (C) DL-Compound | — | — | ⅛ | 2/4 | — |
| (C) L-Compound | ⅛ | ⅛ | ⅛ | 2/4 | — |

*$p < 0.05$;
**$p < 0.01$

TABLE 4

| Drug Used | Route of Administration | Minimum Effective Dose (mg/kg) | | |
|---|---|---|---|---|
| | | (1) | (2) | (3) |
| Aniracetam | i.p. | 3 | 30 | 30 |
| | p.o. | 50 | 50 | 50 |
| DL-Compd | i.p. | 1 | 10 | 30 |
| | p.o. | 30 | 10 | 30 |
| D-Compd | i.p. | 0.3 | 10 | 3 |
| | p.o. | 10 | 10 | 10 |

(1), (2) and (3) in Table 4 show the minimum effective dose scopolamine, electric shock and an excess $CO_2$, respectively.

It is apparent that the compounds of the present invention exhibit useful effects.

Acute Toxicity

N-(2-Pyrrolidone-5-carbonyl)-piperidine was given intraperitoneally and orally to male mice and the toxic symptoms were observed for 7 days.

No animals died after the intraperitoneal injection of 1,000 mg/kg and essentially no toxic symptoms were observed.

After oral administration of 3000 mg/kg, no animals died and no toxic symptoms were observed.

It is apparent that the compounds of the present invention are safe.

Tables 5 and 6 below, set forth the results when N-(5-oxo-D-prolyl) piperidine was used and as a reference drug aniracetam was used. The minimum effective dose by intraperitoneal and oral administration giving a significant effect is set forth in Table 3 and in part (1) in Table 6 below.

It is noted that Tables 5 and 6 below report in parts (1), (2) and (3) the results of three tests, namely (1) Improving effect on memory disruption induced by scopolamine;

(2) Improving effect on memory disruption induced by electric shock; and (3) Improving effect on memory disruption induced by an excess of $CO_2$.

All minimum effective doses in Tables 2, 4 and 6 are given as effective doses (mg/kg) showing significant improving effect at $p < 0.05$ by $\chi^2$-test. Parts (2) and (3) are described below.

It is apparent that the compounds of the present invention show desirable activity.

Improving Effect on Memory Disruption Induced by Electric Shock

The same method as that in the scopolamine-induced memory disruption was used. After acquisition session, rats were subjected to an electric shock and, after recovery from convulsion, the drug was administered intraperitoneally or orally. The retention session was conducted after 1 and 3 hours, respectively.

The rate of positive reaction at that time was measured and minimum doses showing the significant improving effect are given in part (2) of Table 4 above for the compounds of Examples 3 and 72. In addition, according to the procedures described above, N-2-(2-pyrrolidone-5-carbonyl) piperidine was tested and the results are set forth in part (2) of Table 4 above.

Part (2) of Table 6 below sets forth the test results showing a significant effect in (2) for N-(5-oxo-D-prolyl) piperidine.

Memory Disruption by an Excess of $CO_2$

The drug was given intraperitoneally or orally and after 30 and 60 minutes, respectively, rats were placed for 12 seconds in a chamber filled with $CO_2$ gas. After 3 minutes, they were moved to a two compartment shuttle box, subjected to an active avoidance response and escape response using buzzer as a conditioned stimulation, and the rate of positiveness (numbers of positive animals/numbers of all animals used) of response acquiring test after six trials was measured and minimum effective doses showing the significant improving effect are given in part (3) of Tables 2, 4 and 6 for the compounds referred to in these Tables.

TABLE 5

| Drug Used | Rate of Positive Reaction (Numbers of Positive Animals/Numbers of Animals Used) Doses (mg/kg; i.p.) | | | | |
|---|---|---|---|---|---|
| | 0.3 | 1 | 3 | 10 | 30 |
| Aniracetam | — | ⅛ | ⅛* | ⅛* | 4/8 |
| D-Compound | ⅛* | 6/8** | ⅛ | — | — |

*$p < 0.05$;
**$p < 0.01$

TABLE 6

| Drug Used | Route of Administration | Minimum Effective Dose (mg/kg) Test Numbers | | |
|---|---|---|---|---|
| | | (1) | (2) | (3) |
| Aniracetam | i.p. | 3 | 30 | 30 |
| | p.o. | 50 | 50 | 50 |

| | Route of Admini- | Minimum Effective Dose (mg/kg) Test Numbers | | |
|---|---|---|---|---|
| Drug Used | stration | (1) | (2) | (3) |
| D-Compound | i.p. | 0.3 | 10 | 3 |
| | p.o. | 10 | 10 | 10 |

It is apparent that the compounds of the present invention exhibit marked effects.

Acute Toxicity

Male mice were given the compounds of the present invention (examples 3 and 72) intravenously and orally and, after seven days, were observed for signs of toxicity.

When 1000 mg/kg was intravenously injected, no deaths were observed from either compound and no significant toxic signs were observed.

In the case of oral administration, no deaths were observed after administration of 3000 mg/kg and no toxic signs were observed.

N-(2-pyrrolidone-5-carbonyl)-piperidine was given intraperitoneal and orally to male mice. The mice were observed for 7 days for toxic symptoms.

No animals died after the intraperitoneal injection of 1000 mg/kg and no significant toxic symptoms were observed. After oral administration, no animals died at a dose of 3000 mg/kg and no toxic symptoms were observed.

N-(5-oxo-D-prolyl) piperidine was given intravenously and orally to male mice and during seven days, the mice were observed for toxic symptoms. No animals died after intravenous administration of 1000 mg/kg and no significant toxic symptoms were observed. After oral administration, no animals died and no toxic symptoms were observed at a dose of 3000 mg/kg.

It is apparent that the compounds of the present invention are quite safe and substantially non-toxic.

The following nonlimitative formulation examples more particularly illustrate formulations utilizing the compounds of the present invention.

FORMULATION EXAMPLE A

N-(2-pyrrolidone-5-carbonyl) piperidine was dissolved in physiological saline solution to make 5% (w/v) solution. The solution was filtered using a membrane filter, filled in ampules of, say, 1 ml, 2 ml, 5 ml, 10 ml or 20 ml, sterilized in a autoclave and injectable preparations were manufactured.

FORMULATION EXAMPLE B

N-(2-pyrrolidone-5-carbonyl) piperidine (D-isomer) was dissolved in a physiological saline solution to make a 5% (w/v) solution. This was filtered using a membrane filter, filled in ampoules of, say, 1 ml, 2 ml, 5 ml, 10 ml, or 20 ml, and sterilized in an autoclave to manufacture injectable preparations.

FORMULATION EXAMPLE C

N-(2-pyrrolidone-5-carbonyl) piperidine (250 mg), 181.2 mg of lactose, 77.6 mg of starch, 40.0 mg of crystalline cellulose, 17.1 mg of methylcellulose, 2.9 mg of water-containing silicone dioxide, and 1.2 mg of magnesium stearate were taken and made into tablets by conventional manner.

FORMULATION EXAMPLE D

N-(2-pyrrolidone-5-carbonyl) piperidine (D-isomer) 500 mg, 124.0 mg of lactose, 1.3 mg of water-containing silicone dioxide, 12.8 mg of polyvinyl alcohol, and 1.9 mg of magnesium stearate were taken and made into hard capsule preparations by conventional manner.

What is claimed is:

1. A compound of the formula:

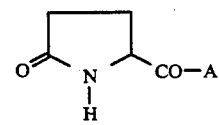

(I)

or pharmaceutically acceptable acid addition salt thereof wherein A is azetidino, pyrrolidino, piperidino, azepino, azocino, piperazino, homopiperazino, homopiperidino or tetrahydroisoquinolino, unsubstituted or substituted by a substituent selected from the group consisting of alkyl, diarylalkyl, aralkyl, aryl, hydroxyalkyl, hydroxy, alkanoyl of 1 to 7 carbon atoms, aralkylcarbonyl, aralkyloxycarbonyl, aralkenylcarbonyl, arylcarbonyl, heterocyclylcarbonyl, alkoxycarbonyl, aminoalkyl, aminoalkylcarbonyl, aminocarbonyl, carbamoylalkyl, carbamoylalkylcarbonyl, oxo, heterocyclyl, aryloxyalkyl, and alkanoylamino, wherein said alkyl is a lower alkyl moiety, said alkenyl is a lower alkenyl moiety, said alkoxy is a lower alkoxy moiety, said aryl has 6 to 14 carbon atoms and is unsubstituted or substituted by 1 or more of the same or different substituents selected from the group consisting of lower alkyl, lower alkoxy, aryl lower alkyloxy, lower alkanoyl, lower alkoxycarbonyl, halo, halo lower alkyl, nitro and methylenedioxy wherein aryl is as above defined; said heterocyclyl is pyridyl, thienyl, furyl, morpholino or thiomorpholino; and wherein when one of the above substituents contains an amino moiety, said amino moiety is straight chain amino or pyrrolidino, piperidino, azepino, piperazino, morpholino or thiomorpholino, said amino moiety being unsubstituted or substituted by one or more substituents selected from the group consisting of lower alkyl, aryl lower alkyl, aryl lower alkyloxycarbonyl and carbamoyl wherein aryl is as above defined provided that A is not 2,2,6,6-tetramethylpiperidino, 3-hydroxypiperidino, 4-hydroxypiperidino, 2-aminocarbonyl-pyrrolidino, 2-carbamoylpyrrolidino, 2-methoxycarbonylpyrrolidino, 2-carboxypyrrolidino, 2-(2-carboxypyrrolidino)carbonylpyrrolidino, unsubstituted pyrrolidino, piperidino, indolino, isoindolino or imidazolyl.

2. A compound according to claim 1 in the form of the D-isomer.

3. A compound according to claim 2 wherein A is substituted by pyrrolidino, piperidino, azepino, piperazino, morpholino or thiomorpholino.

4. A compound according to claim 1 wherein the aralkyl moiety contains 7-12 carbon atoms.

5. A compound according to claim 1 in the form of a pharmaceutically acceptable acid addition salt.

6. The compound according to claim 1 which is 4-morpholinocarbonylmethyl-1-(2-pyrrolidone-5-carbonyl)-piperazine; 4-ethoxycarbonyl-1-(2-pyrrolidone-5-carbonyl)piperazine; 4-morpholinoacetyl-1-(2-pyrrolidone-5-carbonyl)piperazine; 4-(4-methylbenzyl)-1-(2-pyrrolidone-5-carbonyl)piperazine; 4-benzyl-N-(2- pyrrolidone-5-carbonyl)piperidine; 4-hydroxy-N-(2-pyrrolidone-5-carbonyl)piperidine; 1-(2-pyrrolidone-5-carbonyl)-4-thiomorpholinocarbonylmethylpiperazine; or D-(+)-4-morpholinocarbonylmethyl-1-(2-pyrrolidone-5-carbonyl)piperazine maleate.

7. The compound according to claim 1 which is D-(+)-4-morpholinocarbonylmethyl-1-(2-pyrrolidone-5-carbonyl)piperazine maleate.

8. N-(5-oxo-D-prolyl)piperidine.

9. A pharmaceutical composition useful for effecting nootropic action in humans and animals which comprises a therapeutically effective amount of a compound of the formula:

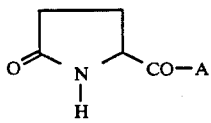
(I)

or pharmaceutically acceptable acid addition salt thereof wherein A is azetidino, pyrrolidino, piperidino, azepino, azocino, piperazino, homopiperazino, homopiperidino or tetrahydroisoquinolino, unsubstituted or substituted by a substituent selected from the group consisting of alkyl, diarylalkyl, aralkyl, aryl, hydroxyalkyl, hydroxy, alkanoyl of 1 to 7 carbon atoms, aralkylcarbonyl, aralkyloxycarbonyl, aralkenylcarbonyl, arylcarbonyl, heterocyclylcarbonyl, alkoxycarbonyl, aminoalkyl, aminoalkylcarbonyl, aminocarbonyl, carbamoylalkyl, carbamoylalkylcarbonyl, oxo, heterocyclyl, aryloxyalkyl, and alkanoylamino, wherein said alkyl is a lower alkyl moiety, said alkenyl is a lower alkenyl moiety, said alkoxy is a lower alkoxy moiety, said aryl has 6 to 14 carbon atoms and is unsubstituted or substituted by 1 or more of the same or different substituents selected from the group consisting of lower alkyl, lower alkoxy, aryl lower alkyloxy, lower alkanoyl, lower alkoxycarbonyl, halo, halo lower alkyl, nitro and methylenedioxy wherein aryl is as above defined; said heterocyclyl is pyridyl, thienyl, furyl, morpholino or thiomorpholino; and wherein when one of the above substituents contains an amino moiety, said amino moiety is straight chain amino or pyrrolidino, piperidino, azepino, piperazino, morpholino or thiomorpholino, said amino moiety being unsubstituted or substituted by one or more substituents selected from the group consisting of lower alkyl, aryl lower alkyl, aryl lower alkyloxycarbonyl and carbamoyl wherein aryl is as above defined, in combination with a pharmaceutically acceptable carrier.

10. A composition according to claim 9 wherein the compound is in the form of the D-isomer.

11. A composition according to claim 10 wherein A is substituted by pyrrolidino, piperidino, azepino, piperazino, morpholino or thiomorpholino.

12. A composition according to claim 9 wherein the aralkyl moiety contains 7-12 carbon atoms.

13. A composition according to claim 9 wherein the compound is in the form of a pharmaceutically acceptable acid addition salt.

14. A composition according to claim 9 wherein the compound is 4-morpholinocarbonylmethyl-1-(2-pyrrolidone-5-carbonyl)-piperazine; 4-ethoxycarbonyl-1-(2-pyrrolidone-5-carbonyl)piperazine; 4-morpholinoacetyl-1-(2-pyrrolidone-5-carbonyl)piperazine; 4-(4-methylbenzyl)-1-(2-pyrrolidone-5-carbonyl)piperazine; 4-benzyl-N-(2-pyrrolidone-5-carbonyl)piperidine; 4-hydroxy-N-(2-pyrrolidone-5-carbonyl)-piperidine; 1-(2-pyrrolidone-5-carbonyl)-4-thiomorpholinocarbonylmethylpiperazine; or D-(+)-4-morpholinocarbonylmethyl-1-(2-pyrrolidone-5-carbonyl)piperazine maleate.

15. The composition according to claim 9 wherein the compound is D-(+)-4-morpholinocarbonylmethyl-1-(2-pyrrolidone-5-carbonyl)piperazine maleate.

16. A method of effecting nootropic action in humans and animals which comprises administering to a human or animal in need thereof a therapeutically effective amount of a compound of the formula:

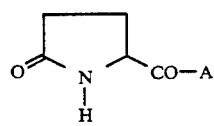
(I)

or pharmaceutically acceptable acid addition salt thereof wherein A is azetidino, pyrrolidino, piperidino, azepino, azocino, piperazino, homopiperazino, homopiperidino or tetrahydroisoquinolino, unsubstituted or substituted by a substituent selected from the group consisting of alkyl, diarylalkyl, aralkyl, aryl, hydroxyalkyl, hydroxy, alkanoyl of 1 to 7 carbon atoms, aralkylcarbonyl, aralkyloxycarbonyl, aralkenylcarbonyl, arylcarbonyl, heterocyclylcarbonyl, alkoxycarbonyl, aminoalkyl, aminoalkylcarbonyl, aminocarbonyl, carbamoylalkyl, carbamoylalkylcarbonyl, oxo, heterocyclyl, aryloxyalkyl, and alkanoylamino, wherein said alkyl is a lower alkyl moiety, said alkenyl is a lower alkenyl moiety, said alkoxy is a lower alkoxy moiety, said aryl has 6 to 14 carbon atoms and is unsubstituted or substituted by 1 or more of the same or different substituents selected from the group consisting of lower alkyl, lower alkoxy, aryl lower alkyloxy, lower alkanoyl, lower alkoxycarbonyl, halo, halo lower alkyl, nitro and methylenedioxy wherein aryl is as above defined; said heterocyclyl is pyridyl, thienyl, furyl, morpholino or thiomorpholino; and wherein when one of the above substituents contains an amino moiety, said amino moiety is straight chain amino or pyrrolidino, piperidino, azepino, piperazino, morpholino or thiomorpholino, said amino moiety being unsubstituted or substituted by one or more substituents selected from the group consisting of lower alkyl, aryl lower alkyl, aryl lower alkyloxycarbonyl and carbamoyl wherein aryl is as defined above, in combination with a pharmaceutically acceptable carrier.

17. A method according to claim 16 wherein the compound is in the form of the D-isomer.

18. A method according to claim 17 wherein A is substituted by pyrrolidino, piperidino, azepino, piperazino, morpholino or thiomorpholino.

19. A method according to claim 16 wherein the aralkyl moiety contains 7-12 carbon atoms.

20. A method according to claim 16 wherein the compound is in the form of a pharmaceutically acceptable acid addition salt.

21. A method according to claim 17 wherein the compound is 4-morpholinocarbonylmethyl-1-(2-pyrrolidone-5-carbonyl)-piperazine; 4-ethoxycarbonyl-1-(2-pyrrolidone-5-carbonyl)piperazine; 4-morpholinoacetyl-1-(2-pyrrolidone-5-carbonyl)piperazine; 4-(4-methylbenzyl)-1-(2-pyrrolidone-5-carbonyl)piperazine; 4-benzyl-N-(2-pyrrolidone-5-carbonyl)piperidine; 4-hydroxy-N-(2-pyrrolidone-5-carbonyl)piperidine; 1-(2- pyrrolidone-5-carbonyl)-4-thiomorpholinocarbonylmethylpiperazine; or D-(+)-4-morpholinocarbonylmethyl-1-(2-pyrrolidone-5-carbonyl)piperazine maleate.

22. A method according to claim 16 wherein the compound is D-(+)-4-morpholinocarbonylmethyl-1-(2-pyrrolidone-5-carbonyl)piperazine maleate.

23. A pharmaceutical composition useful for effecting nootropic action in humans and animals which comprises a therapeutically effective amount of N-(5-oxo-D-prolyl)piperidine, in combination with a pharmaceutically acceptable carrier.

24. A method of effecting nootropic action in humans and animals which comprises administering to a human or animal in need thereof a therapeutically effective amount of N-(5-oxo-D-prolyl)piperidine.

* * * * *